United States Patent [19]

Tohmatsu et al.

[11] 4,132,767

[45] Jan. 2, 1979

[54] PREPARATION OF α-L ANTIBODY, PURIFICATION OF α-L ANTIGEN AND REAGENT FOR DETECTION OF α-L ANTIBODY AND α-L ANTIGEN

[75] Inventors: Jun-ichi Tohmatsu, Tokyo; Tomiaki Morimoto, Fuchu; Emiko Kishi, Ohmiya, all of Japan

[73] Assignee: Eisai Co., Ltd., Tokyo, Japan

[21] Appl. No.: 783,460

[22] Filed: Mar. 31, 1977

[30] Foreign Application Priority Data

| Apr. 5, 1976 [JP] | Japan | 51-37928 |
| Apr. 5, 1976 [JP] | Japan | 51-37929 |
| Apr. 5, 1976 [JP] | Japan | 51-37930 |
| Apr. 5, 1976 [JP] | Japan | 51-37931 |

[51] Int. Cl.$^2$ .................... A61K 43/00; G01N 33/16
[52] U.S. Cl. ........................ 424/1; 252/408; 23/230 B; 424/8; 260/112 R
[58] Field of Search ............. 424/118; 23/230 B; 252/408; 260/112 R

[56] References Cited

U.S. PATENT DOCUMENTS

| 3,663,684 | 5/1972 | Freedman et al. | 424/1 |
| 3,697,638 | 10/1972 | Hansen | 424/1 |
| 3,823,126 | 7/1974 | Bjorklund | 260/112 R |
| 3,867,363 | 2/1975 | Hansen | 260/112 R |
| 3,956,258 | 5/1976 | Hansen | 260/112 R |
| 3,960,827 | 6/1976 | Bjorklund | 260/112 R |

Primary Examiner—Leland A. Sebastian
Assistant Examiner—Christine M. Nucker
Attorney, Agent, or Firm—Wenderoth, Lind & Ponack

[57] ABSTRACT

Process for the preparation of a novel α-L antibody comprising immunizing an animal other than a human with the α-L antigen or α-L antigen/α-L antibody complex, and collecting antiserum from the animal; a method for the purification of α-L antigen comprising subjecting the material containing the α-L antigen to the density gradient centrifugation, and collecting a fraction having a buoyant density less than 1.1 g/ml; a reagent comprising α-L antigen; and a reagent comprising α-L antibody for detection of the α-L antigen and the α-L antibody, such detection being useful for the diagnosis of liver diseases and examination of the blood for blood transfusion.

11 Claims, No Drawings

PREPARATION OF α-L ANTIBODY, PURIFICATION OF α-L ANTIGEN AND REAGENT FOR DETECTION OF α-L ANTIBODY AND α-L ANTIGEN

BACKGROUND OF THE INVENTION

This invention relates to a novel antigen associated with liver diseases and a process for the preparation of an antibody thereof to be used for detection of α-L antigen and α-L antibody.

This invention also relates to a reagent for detection of the α-L antigen and the α-L antibody comprising the α-L antibody.

Further, this invention relates to a reagent for detection comprising α-L antigen, and which may be used for the detection of α-L antigen and α-L antibody.

Furthermore, this invention relates to a method for the purification of α-L antigen which is a novel antigen associated with liver diseases.

DESCRIPTION OF THE PRIOR ART

Up to now, it has been well known that there are HB antigens (HBs, HBc, e) and HA antigens which are found in patients suffering from hepatitis, α-fetoprotein which is found in patients suffering from primary liver cancer, and the like, as antigens associated with the liver diseases. The detection of these antigens and their corresponding antibodies is used for the diagnosis of liver diseases and examination of the blood for blood transfusions. However, since there are, in the examination of liver diseases, many cases which are negative to said antigens and antibodies, it is not sufficient to use only an examination for detection using these antigens and antibodies.

SUMMARY OF THE INVENTION

The inventors have discovered a novel α-L antigen (called as Arai-antigen) and its antibody associated with liver diseases during a study of the serum of patients suffering from liver diseases. The α-L antigen has the following properties.

(1) Molecular weight: About 1,000,000 [It is eluted at almost the same fraction as IgM (molecular weight is about 900,000–1,000,000) by a column chromatography with Bio.gel A-1.5 m (Trade Mark for BIORED Laboratories)]

(2) Electrophoretic mobility: $\beta$—$\alpha_2$ globulin region (this is an intermediate value between HBs antiben and α-fetoprotein)

(3) Isoelectric point: PI = 5.04 (activity of the α-L antigen was shown in the range from 4.22 to 5.68) by measuring with Ampholien column.

(4) Buoyant density: d = 1.08 g/ml in solution of cesium chloride; and d = 1.03 g/ml in solution of sucrose.

(5) Formation of complex: A precipitable complex is formed with dextran sulfate in the presence of magnesium chloride, exhibiting lipoprotein-like properties.

(6) Staining: The α-L antigen/antibody precipitated line in agar gel can be stained with Sudan black B.

(7) Thermostability: Antigenic properties in the serum are still kept at 56° C. for 30 minutes.

(8) Form (as an antigen/antibody complex): Spheric particle of about 300 Å in diameter.

The inventors studied the frequency at which α-L antigen and antibody are detected in the serum of patients suffering from various liver diseases, HBs antigen-positive carrier serum, and the serum of a normal human, and the relationship between the α-L antigen and antibody of the present invention and the known antigens and antibodies associated with liver diseases, i.e. HBs antigen system, e-antigen system and α-fetoprotein (hereinafter referred to α-FP). The results are shown in the following table. In this table, HBs antigen was examined by the IAHA method; HBs antibody was examined by the PHA method, and the others were examined by the MO method, respectively.

Table

| Diagnosis | Number examples | α-L | Numbers of examples | HBS Ag(+) | HBS Ab(+) | e Ag(+) | e Ab(+) | α-F8 Ag(+) |
|---|---|---|---|---|---|---|---|---|
| Liver Cancer | 39 | Ag(+) | 9 | 6 | 0 | 1 | 0 | 4 |
|  |  | Ab(+) | 1 | 0 | 0 | 0 | 0 | 1 |
|  |  | Ag,Ab(−) | 29 | 15 | 3 | 0 | 0 | 12 |
| Cirrhosis of the liver | 35 | Ag(+) | 6 | 2 | 0 | 0 | 0 | 0 |
|  |  | Ab(+) | 6 | 5 | 0 | 0 | 2 | 0 |
|  |  | Ag,Ab(−) | 23 | 16 | 2 | 0 | 0 | 0 |
| Chronic hepatitis | 40 | Ag(+) | 3 | 1 | 1 | 0 | 1 | 0 |
|  |  | Ab(+) | 0 | 0 | 0 | 0 | 0 | 0 |
|  |  | Ag,Ab(−) | 37 | 19 | 1 | 1 | 0 | 0 |
| Acute hepatitis | 40 | Ag(+) | 4 | 3 | 0 | 0 | 1 | 0 |
|  |  | Ab(+) | 4 | 2 | 1 | 0 | 1 | 0 |
|  |  | Ag,Ab(−) | 32 | 15 | 8 | 2 | 4 | 0 |
| HBs Ag(+) blood donor | 20 | Ag(+) | 0 | 0 | 0 | 0 | 0 | 0 |
|  |  | Ab(+) | 1 | 1 | 0 | 0 | 0 | 0 |
|  |  | Ag,Ab(−) | 19 | 19 | 0 | 0 | 2 | 0 |
| Normal human | 20 | Ag(+) | 0 | 0 | 0 | 0 | 0 | 0 |
|  |  | Ab(+) | 0 | 0 | 0 | 0 | 0 | 0 |
|  |  | Ag,Ab(−) | 20 | 0 | 4 | 0 | 0 | 0 |

As indicated in the above table, the α-L antigen shows high positivity to cancer of the liver and cirrhosis of the liver, and the existence of the α-L antigen is detected in chronic hepatitis and acute hepatitis. However, the α-L antigen cannot be detected in the HBs antigen positive blood donor and the normal human. The α-L antibody shows high positivity in cirrhosis of the liver and is also detected in the HBs antibody positive blood donor. About 60% of the serum positive to α-L antigen and α-L antibody are accompanied by the HBs antigen-antibody system. In case of the serum of liver cancer, about 45% of the serums positive to α-L antigen are accompanied with α-FP. On the other hand, about 25% of the serums positive to α-L antigen are utterly regardless of the known antigen-antibody system.

Accordingly, α-L antigen and α-L antibody are very much associated with liver diseases. The detection of the α-L antigen and α-L antibody is useful for diagnosis of liver diseases and examination of the blood for blood transfusions.

One of objects of this invention is to provide a novel α-L antigen associating liver diseases for the detection of α-L antigen and α-L antibody.

Another object of this invention is to provide a process for the preparation of the α-L antibody, which comprises immunizing an animal other than a human with the α-L antigen or the α-L antigen/antibody complex to collect antiserum from the animal.

Further object of this invention is to provide a reagent comprising the α-L antibody for detection of the α-L antigen and the α-L antibody.

Moreover, an object of this invention is to provide a reagent comprising the α-L antigen for detection of α-L antigen and α-L antibody.

Furthermore, an object of this invention is to provide a method for the purification of the α-L antigen.

DESCRIPTION OF THE PREFERRED EMBODIMENTS

The α-L antibody is prepared by immunizing an animal other than a human with the α-L antigen or the α-L antigen/antibody complex, to collect the antiserum.

The α-L antigen can be used in a form of α-L antigen positive serum or ascites per se, or in a purified form of the serum or the ascites by a protein or lipoprotein separation method. As such separation method, there is used a conventional method which is employed in an immunological field. The said methods include, for example, methods of density gradient centrifugation, salting out, electrophoresis, gel filtration, affinity chromatography, isoelectric focusing, ultra-filtration, Cohn's fraction, dextran sulfate precipitation method, and a method which comprises adding antiserum against impurities other than α-L antigen to remove the impurities, etc.

The α-L antigen/antibody complex may be obtained as precipitates by, for example, mixing the α-L antigen solution with the α-L antibody solution.

As animals for immunization, there may be mentioned, for example rabbit, guinea-pig, goat, horse, cow, etc.

When immunization is carried out, it is preferable, in order to obtain the antiserum of high antibody activity, to carry it out with the α-L antigen or the α-L antigen/antibody complex which was emulsified using the Freund complete adjuvant, and to carry such imunization out not only once, but several times.

The resulting antiserum can be purified by the immunoadsorption method using the serum of a normal human, the affinity chromatography, and the like.

Besides the method which comprises preparing α-L antibody by immunizing an animal as mentioned above, there is a method which comprises purifying the α-L antibody by the α-L antibody-positive human serum. However, this method cannot produce a large amount of the α-L antibody.

Using the α-L antibody obtained according to this invention, α-L antigens and α-L antibodies are detected by a conventional method such, for example, as the Ouchterlony method (MO), the single radial immuno diffusion method (SRID), the immuno electrophoresis method (IES, IEP), the radioimmuno assay method (RIA), the enzyme-linked immuno solvent assay method (ELISA), the complement fixation method (CF), the reverse passive hemagglutination method (RPHA) or the immune adherence hemagglutination method (IAHA).

A reagent for detection comprising the α-L antigen of this invention can be used for a conventional immunological method for detection which uses an antigen-antibody reaction. The method for the detection includes a method using the antigen per se, and a method using the treated antigen. A reagent for detection comprising α-L antigen of this invention includes both α-L antigen per se and the treated α-L a antigen.

The α-L antigen per se is used, when the detection is carried out by methods such as the Ouchterlony method (MO), the immunoelectrophoresis method (IES, IEP), complement fixation method (CF), the immuneadherence hemagglutination method (IAHA), and the like.

The treated α-L antigen is used when the detection is carried out by methods such as a single radial immuno diffusion method (SRID), radioimmuno assay method (RIA), enzyme-linked immuno solvent assay method (ELISA), passive hemagglutination method (PHA), and the like.

In the case of the single radial immunodiffusion method (SRID), there can be used the treated α-L antigen which was prepared by dissolving α-L antigen together with a supporting medium, and solidifying the solution in a form of plate. Such a supporting medium may involve, for example, agar, agarose, starch, polyacrylamide gel, and the like. The gel plate may be obtained from said supporting medium and α-L antigen, by a conventional method. For example, a supporting medium is dissolved under heat in a buffer solution, α-L antigen is then added to the solution, and the whole is mixed together. The resulting solution is poured onto a glass plate or into a plastic vessel, and then cooled to solidify. In order to apply the serum to be examined, a hole is made in the resulting gel plate.

In the case of the passive hemagglutination method (PHA), there is used the α-L antigen which was prepared by binding α-L antigen to fine particles. As the fine particles, conventional materials can be used. Especially preferable are fine particles which include the erythrocytes of mammals and birds. There may be used particles having a diameter of about 1–10 μm of polystyrene latex, polyester latex, polyvinylchloride, bentonite, glass beads and the like. The conventional binding reagents may be used in order to the bind α-L antigen to fine particles. Such reagents include, for example, glutaraldehyde, formaldehyde, tannic acid, bisdiazotized benzidine, chromic chloride, carbodiimide and the like.

In the case of a radioimmuno assay method (RIA), there is used the α-L antigen labelled with an isotope. The labellation may be performed by a conventional method such as the Chloroamine T method using $^{125}I$, $^{131}I$.

In the case of the enzyme-linked immuno solvent assay method (ELISA), α-L antigen bound to enzyme is used. There may be used, as such an enzyme, glucoseoxydaze, alkali phosphataze, peloxydaze and the like, for example. Glutaraldehyde is usually used as a binder.

The α-L antigen and α-L antibody can be detected by a conventional method, using the abovementioned reagents for detection comprising α-L antigen. In most cases, the reagent for detection comprising α-L antigen is used for detecting α-L antibody. This reagent can also be used to detect α-L antibody by adopting the inhibited reaction wherein α-L antibody is used in each method. In each method, there may be suitably and additionally used other reagents such as a complement, erythrocyte, buffer solution, α-L antibody and the like, if necessary.

The above description of the reagent for detection comprising the α-L antigen may be applied literally to the reagent for detection which comprises the α-L antibody according to this invention, provided that the term "α-L antibody" is substituted in place of the term "α-L antigen".

The method for purification of α-L antigen according to this invention is performed by subjecting a material containing α-L antigen to the density gradient centrifugation, and collecting a fraction of a buoyant density less than 1.1 g/ml. preferably 1.03–1.08 g/ml.

By means of said operation, the α-L antigen can be separated from a large part of impure protein component and other antigens associating liver diseases, since the α-L antigen has a very small buoyant density.

As a material containing α-L antigen which may be used in this invention, there can be mentioned every kind of substance containing α-L antigen such as α-L antigen positive serum and ascites, and the like.

As a medium for the density gradient centrifugation, it is possible to use conventional mediums such as cesium chloride, cesium bromide, potassium bromide, lithium bromide, lithium chloride, sodium chloride, glycerol, sucrose, and the like.

In carrying out a method for the purification of this invention, there can be used, in a form of combination, other methods for separating protein or lipoprotein fraction, such for example as method of salting out, electrophoresis, gel filtration, affinity chromatography, isoelectric focusing, ultra-filtration, Cohn's fraction, dextran sulfate purification method, or a method which comprises adding antibodies against the impurities other than α-L antigen to remove the impurities, and the like, whereby more purified α-L antigen is obtained.

The method of this invention is especially excellent as a method for purifying, at first, the α-L antigen from the raw materials such as serum, ascites and the like. The method may be used also for further purification of the α-L antigen which was previously purified by an other purification method.

Following examples and experiments will serve to illustrate the invention, but it should be construed that the invention is not restricted by these examples and experiments.

EXAMPLE 1

By centrifugating 100 ml of the α-L antigen-positive serum for 20 minutes at 10,000 r.p.m., the supernatant was recovered. Powdery cesium chloride was added to this supernatant in a ratio of 0.3 g/ml to dissolve the whole. The resulting solution was subjected to the density gradient centrifugation for 40 hours at 40,000 r.p.m. The top fraction having a buoyant density less than 1.1 g/ml was collected, and dialyzed respectively with distilled water and saline overnight. The resulting solution was concentrated to about 5 times the concentration of the original solution, using Amicon Diaflow-XM-50 (TM, Amicon Co.), to obtain the α-L antigen solution. The resulting α-L antigen forms a complex with the α-L antibody, and no other antigens associated with liver diseases were recognized, such as an HBs antigen, e-antigen, the α-FP and the like by the MO method. The specific activity of the α-L antigen was increased about 30 times. This α-L antigen is useful as a reagent for detection.

EXAMPLE 2 using 100 ml of the α-L antigen-positive ascites, the α-L antigen solution was obtained by the same procedure as described in Example 1. The density gradient in the range of 1.05–1.2 g/ml was formed previously in a cellulose tube, using a solution wherein cesium chloride was dissolved in 0.01 M tris hydrochloric acid buffer solution. The α-L antigen solution was added on top of the upper layer in the tube to form several layers. The whole was then subjected to a density gradient centrifugation for 24 hours at 40,000 r.p.m. The α-L antigen-positive fraction was collected and dialyzed first with distilled water and then with the tris hydrochloric acid buffer solution overnight, respectively. The resulting solution was then concentrated to above 5 time the concentration of the original solution, using Amicon Diaflow-XM-50. The resulting α-L antigen forms a complex with α-L antibody, and no other antigens associated with liver diseases were recognized such as an HBs antigen, e-antigen, α-FP and the like by the MO method. The specific activity of α-L antigen was increased about 100 times. This α-L antigen can be useful as a reagent for detection.

EXAMPLE 3

The α-L antigen solution prepared by Example 1 was emulsified after the addition of a Freund complete adjuvant in a ratio of 1:1. milliliter of the emulsion was divisionally injected into the back of a rabbit by a subcutaneous and an intracutaneous injection and also into the foot pads (sole of leg), so that the rabbit was immunized. One week after said first immunization, the second immunization was achieved by the same manner with the same amount of the emulsion as in the first immunization. One month after said first immunization, the third immunization was achieved with a double amount of the emulsion as was used in the first immunization. One week after the last immunization, the blood was collected several times, and the serum was separated from an blood. To this serum, the equivalent amount of the serum of a normal human was added. The mixture was allowed to stand for one hour at 37° C. and overnight at 4° C. This mixture of serum was centrifugated at 10,000 r.p.m. for 10 minutes to recover the supernatant. The resulting antiserum containing the α-L antibody reacts exceptionally with only α-L antigen, but does not react with the other antigens associated with liver disease such as HBs antigen, e-antigen, α-FP, and the like, as well as the serum of a normal human.

The antiserum comprising this α-L antibody may be used for the reagent for detection according to this invention.

EXAMPLE 4

A Freund complete adjuvant was added to a solution of the α-L antigen prepared as in Example 2 in a ratio of 1:1 to emulsify the whole. An amount of 0.5 ml of the emulsion was divisionally injected into the back of a guinea-pig by a subcutaneous and an intracutaneous injection, and also to the foot pads, so as to immunize the guinea-pig. Following the same procedure as in Example 3, the antiserum comprising the α-L antibody was obtained.

The resulting antiserum reacts exceptionally with only α-L antigen, but does not react with the other antigens associated with liver disease such as HBs-antigen, e-antigen, α-FP, and the like, as well as the serum of a normal human.

The antiserum comprising this α-L antibody may be used for the reagent for detection according to this invention.

EXAMPLE 5

To 25 ml of the α-L antigen solution obtained in Example 1, there was gradually added 50 ml of the antiserum comprising α-L antibody obtained also in Example 3. The whole was mixed with stirring. The mixture was allowed to stand for one hour at 37° C. and then overnight at 4° C. The mixture was centrifugated at 10,000 r.p.m. for 20 minutes. The α-L antigen/antibody complex was recovered as precipitates. To the precipitates, 0.01 M of tris-aminomethane/hydrochloric acid buffer solution was added, and the mixture was centrifugated, to remove contaminants by washing.

The α-L antigen/antibody complex was suspended in 5 ml of saline, and the suspension was emulsified by adding an equivalent amount of a Freund complete adjuvant. Subsequently, following the same procedure as described in Example 3, The antiserum comprising the α-L antibody was obtained.

The resulting antiserum reacts exceptionally with only α-L antigens, but does not react with antigens associated with liver diseases such as HBs antigen, e-antigen, α-FP, and the like, as well as the serum of a normal human.

EXAMPLE 6

To the antiserum comprising the α-L antibody produced in Example 3, there was added the equivalent amount of 0.05 M phosphate saline buffer solution (pH 7.5). To this solution, there was added an equivalent amount of an aqueous saturated ammonium sulfate solution (pH 6.8). The whole was mixed with stirring. After one hour, the solution was centrifugated at 5,000 r.p.m. for 30 minutes. The resulting precipitates were dissolved in the phosphate saline buffer solution, to obtain a solution having the same volume as that of the original antiserum. One fourth (¼) part by volume of the aqueous saturated ammonium sulfate solution (pH 6.8) was added to the solution. After one hour, the solution was centrifugated at 5,000 r.p.m. for 30 minutes. Further one fourth (¼) part by volume of the aqueous saturated ammonium sulfate solution was added to the resulting supernatant, thereby obtaining 33% ammonium sulfate solution. After one hour, said solution was centrifugated at 5,000 r.p.m. for 30 minutes, and the precipitates were collected. The precipitates were dissolved in 0.01 M tris-aminomethane hydrochloric acid buffer solution (pH 8.0), so as to obtain a solution having the protein concentration of 70 mg/ml. This solution was subjected to the gel filtration with Sephadex G 50 (TM, Pharmacia AB) using said buffer solution, to carry out desalting out and buffering. The resulting solution was concentrated and adjusted to the protein cocentration of 70 mg/ml, using Amicon Diaflow-XM-50. Activated DEAE cellulose was packed in a column of 2.6 cm in diameter and 40 cm in length, using the tris-aminomethane/hydrochloric acid buffer solution. The concentrated solution was added into the column, to adsorb the α-L antibody on the activated DEAE cellulose. The adsorbed α-L antigen was eluted with 0.1 M sodium chloride/tris-aminomethane hydrochloric acid buffer solution (pH 8.0) which was prepared by adding sodium chloride to the tris-aminomethane hydrochloric acid buffer solution. The α-L antibody-positive fraction was isolated and collected. This fraction was then concentrated to the protein concentration of 70 mg/ml using Amicon Diaflow-XM-50. The resulting α-L antibody is used for a reagent for detection.

EXAMPLE 7

The α-L antibody obtained by Example 6 was dissolved in 0.1 M barbital buffer solution (pH 9.0), to adjust an concentration of protein to 10 mg/ml. To this solution, the equivalent amount of bromocyanide-activated Sepharose 4B gel (TM, Pharmacia AB) was added, and the mixture was reacted at 4° C. for 24 hours. Unreacted protein was removed by washing with 0.05 M phosphate saline buffer solution (pH 7.5). The resulting solution was then filled in a column of 1.5 cm in diameter and 20cm in length. The α-L antigen solution according to Example 2 was added to this column.

After removal of the unreacted substance by washing with the phosphate saline buffer solution, there was added 3.5 M sodium iodide solution to the column, to dissociate and elute the α-L antigen. The α-L antigen solution collected was dialized with dialyzed water to remove sodium iodide, and the solution was then concentrated using Amicon Diaflow-XM-50. The resulting α-L antigen can be used as a reagent for detection.

EXAMPLE 8

The α-L antigen solution produced in Example 1 was dissolved in 0.1 M barbital buffer solution (pH 9.0), to adjust the concentration of protein to 10 mg/ml. This solution was added to the equivalent amount of bromocyanide-activated Sepharose 4B gel, and the mixture was reacted at 4° C. for 24 hours. Unreacted protein was removed by washing with 0.05 M phosphate saline buffer solution (pH 7.5). Subsequently, the resulting product was filled in a column of 1.5 cm in diameter and 20 cm in length. The antiserum containing the α-L antibody produced according to Example 3 was added to this column. After removing the unreacted substance by washing with the phosphate saline buffer solution, there was added 3.5 M sodium iodide solution to the column, to dissociate and elute the α-L antigen. The resulting α-L antigen solution was collected and dialyzed with distilled water, to remove sodium iodide, followed by concentrating the solution by the use of Amicon Diaflow-XM-50. The resulting α-L antigen can be used as a reagent for detection.

EXAMPLE 9

The blood of a sheep was collected in a centrifugal tube, and the blood was centrifugated five times at 2,000 r.p.m. for 10 minutes using saline to wash the erythrocytes. To the erthrocytes, there was added 0.15 M phosphate saline buffer solution (pH 7.5), to adjust the concentration of the erythrocyte solution to 5%. To the solution wherein the erythrocytes were floating, there was added 1/5 volume of glutaraldehyde solution adjusted to the concentration of 2.5% with the phosphate saline buffer solution, and the reaction was carried out at room temperature for about 5 hours, under stirring, to fix the erythrocytes. By centrifugating this suspension, there were obtained the fixed erythrocytes, which were then washed several times by means of centrifugation using saline. After adjusting the fixed erythrocytes to a 5% suspension with the phosphate buffer solution, there was added, to the suspension, the equivalent amount of tannic acid solution adjusted to 3 mg/dl with the phosphate saline buffer solution, and agitation was continued for 15 minutes. By centrifugating this suspension, there were obtained the erythrocytes which were treated with tannic acid. The resulting erythrocytes were washed several times by means of centrifugation using saline. To the resulting erythrocytes treated with tannic acid, there was added the phosphate buffer solution, to produce the suspension which contains the erythrocytes in an amount of 5%.

To the suspension containing the erythrocytes, there was added the solution wherein the α-L antibody according to Example 6 was adjusted to a protein concentration of 1 mg/ml by the phosphate saline buffer solution in the same amount, and the whole was mixed. The resulting suspension was agitated for 30 minutes at a room temperature to sensitize it. After centrifugating the suspension, the resulting sensitized erythrocytes were washed several times by means of centrifugation using saline. To the resulting sensitized erythrocytes, there was added the phosphate saline buffer solution, to produce a 7.5% suspension. Adding a minute amount of tymelosal as antiseptic, the solution was preserved at 4° C. The α-L antibody-sensitized erythrocytes of sheep can be used as a reagent for detection in the RPHA method.

EXAMPLE 10

The same procedures as described in Example 9 were repeated, except that the suspension containing the erythrocytes was mixed with an equivalent amount of the solution which was prepared by adjusting the α-L antigen obtained in Example 2 to the protein concentration of 100 μg/ml, using a phosphate saline buffer solution and the mixture was sensitized. The α-L antigen sensitized erythrocytes of sheep can be used as a reagent for detection in PHA a method.

EXAMPLE 11

The α-L antigen according to Example 7 was dissolved in 0.04 M phosphate buffer solution (pH 7.4), and the resulting solution was adjusted to a protein concentration of 1 mg/ml. To 10 μl of the solution, there was added 50 μl of 1 mc $^{125}$I-Na. 10 μl of the solution wherein Chloramine T was dissolved in the phosphate buffer solution in the ratio of 1.5 mg/ml, was added to the above solution, and the resulting solution was agitated for 30 seconds. After addition of 100 μl of the phosphate buffer solution wherein meta sodium bisulfite is dissolved in the ratio of 2 mg/ml, the reaction was stopped. To this reaction solution, there was added 100 μl of the phosphate buffer solution in which potassium iodide was dissolved in the ratio of 10 mg/ml. Immediately, the resulting solution was subjected to gel filtration by using Sephadex G-50, to separte $^{125}$I-labelled α-L antigen and $^{125}$I. The specific radioactivity of the resulting $^{125}$I-labelled α-L antigen was 80 μc/μg.

The $^{125}$I-labelled α-L antigen can be used as a reagent for detection in an RIA method. The region of the detection of α-L antigen varies from 10 mg - 600 mg/ml and the region of the detection of the α-L antibody varies from 30 mg - 1,000 mg/ml.

EXAMPLE 12

The α-L antibody according to Example 8 was dissolved in 0.04 M phosphate buffer solution (pH 7.4), and the resulting solution was adjusted to its protein concentration of 1 mg/ml. To 10 μl of this solution, there was added 50 μl of 1 mc $^{125}$I-Na. To the solution, there was added 10 μl of the solution in which Chloramine T was dissolved in the phosphate buffer solution in a ratio of 1.5 mg/ml, and the resulting solution was agitated for 30 seconds. To the resulting solution, there was added 100 μl of the phosphate buffer solution in which meta sodium bisulfite was dissolved in a ratio of 2 mg/ml, so that the reaction would stop. To this reaction solution, there was added the phosphate buffer solution in which potassium iodide was dissolved in the ratio of 10 mg/ml. The resulting solution was subjected to gel filtration using Sephadex G-50, to separate the $^{125}$I-labelled α-L antibody and $^{125}$I. The specific radioactivity of the resulting $^{125}$I-labelled α-L antibody was 70 μc/μg.

This $^{125}$I-labelled α-L antibody can be used as a reagent for detection in an RIA method. The reagent showed that the region of detection of the α-L antigen varies from 10 mg–600 mg/ml, and the region of the detection of α-L antibody varies from 30 mg–1,000 mg/ml.

EXAMPLE 13

Agarose was dissolved under heat in 0.01 M tris hydrochloric acid buffer solution having a pH of 7.5 (including 0.15 M sodium chloride and 0.1% sodium nitride), so as to include 1.2% agarose. 80 ml of the agarose solution was cooled to about 56° C. and 20 ml of α-L antibody solution according to Example 3 was added to the solution while stirring. The solution was poured into a plastic vessel which was then allowed to cool, thereby obtaining an agarose gel plate of 1 mm in thickness which contained an α-L antibody. On this plate, holes for samples of 3 mm in diameter were made at regular intervals. The resulting product can be used as a reagent for detection in an SRID method.

EXAMPLE 14

The same procedures as described in Example 13 were repeated, except that the α-L antigen obtained in Example 2 was used in place of the α-L antibody solution, thereby obtaining an agarose gel plate containing the α-L antigen of 1 mm in thickness.

The resulting product can be used as a reagent for detection in an SRID method.

Experiment 1

Experiments were carried out for detection of the α-L antigen from the serum of various liver disorders, HBs antigen-positive blood donors, and normal humans. This detection was effected by an MO method using the α-L antibody obtained in Example 3, and by an SRID method using the reagent for detection obtained in Example 13.

Results are shown in the following table.

| Diagnosis | Number of examples of disease | Numbers of examples wherein the α-L antigen was detected | |
|---|---|---|---|
| | | MO method | SRID method |
| Liver cancer | 39 | 9 | 24 |
| Cirrhosis of the | | | |

-continued

| Diagnosis | Number of examples of disease | Numbers of examples wherein the α-L antigen was detected | |
|---|---|---|---|
| | | MO method | SRID method |
| liver | 35 | 6 | 10 |
| Chronic hepatitis | 40 | 3 | 3 |
| Acute hepatitis | 40 | 4 | 10 |
| HBs antigen-positive blood doner | 20 | 0 | 0 |
| Normal human | 20 | 0 | 0 |

Experiment 2

Experiments were carried out for detection of the α-L antibody from the serum of various liver disorders or normal humans, by an SRID method using the reagent for detection obtained in Example 14, and by MO method using the reagent for detection obtained in Example 1, respectively. The results are shown in the following table.

| Diagnosis | Numbers of examples of diseases | Number of examples wherein the α-L antibody was detected | |
|---|---|---|---|
| | | MO method | SRID method |
| Cancer of the liver | 39 | 1 | 2 |
| Cirrhosis of the liver | 35 | 6 | 7 |
| Chronic hepatitis | 40 | 0 | 2 |
| Acute hepatitis | 40 | 4 | 6 |
| Normal human | 40 | 1 | 3 |

Experiment 3

Experiments were carried out for detection of the α-L antigen from the serum of various liver disorders or normal humans, by the SRID method using the reagent for detection obtained in Example 13, and by an IES method using the reagent for detection obtained in Example 3, respectively.

The results are shown in the following table.

| Diagnosis | Number of examples of diseases | Number of examples wherein the α-L antigen was detected | |
|---|---|---|---|
| | | SRID method | IBS method |
| Cancer of the liver | 40 | 21 | 19 |
| Cirrhosis of the liver | 52 | 15 | 14 |
| Chronic hepatitis | 78 | 15 | 15 |
| Acute hepatitis | 44 | 17 | 13 |
| Normal human | 50 | 0 | 0 |

What is claimed is:

1. A process for the preparation of an α-L antibody which comprises immunizing an animal, other than a human, with an α-L antigen or an α-L antigen/α-L antibody complex and collecting antiserum from the animal, said α-L antigens having the following properties:
    (1) Molecular weight: About 1,000,000;
    (2) Electrophoretic mobility: In the $\beta$—$\alpha_2$ globulin region, which is an intermediate value between that of an HBs antigen and an α-fetoprotein;
    (3) Isoelectric point: PI = 5.04, the activity of the α-L antigen was shown in the range of 4.22 to 5.68 by measuring with an Ampholien column;
    (4) Buoyant Density: d = 1.08 g/ml in a solution of cesium chloride; and d = 1.03 g/ml in a solution of sucrose;
    (5) Formation of complex: A precipitable complex is formed with dextran sulfate in the presence of magnesium chloride, exhibiting lipoprotein-like properties;
    (6) Staining: The α-L antigen/antibody precipitated line in agar gel can be stained with Sudan black B;
    (7) Thermostability: The antigenic properties in the serum are maintained at a temperature of 56° C. for 30 minutes; and
    (8) Form (as an antigen/antibody complex): the spherical particles are about 300 Å in diameter.

2. A reagent for detecting α-L antigens and α-L antibodies comprising an α-L antibody prepared by the process of claim 1.

3. A reagent for detecting α-L antigens and α-L antibodies containing the α-L antibody of claim 2 wherein the reagent is in the form of a solidified plate and is prepared by dissolving the α-L antibody together with a supporting medium and solidifying the reagent in the form of a plate.

4. A reagent for detecting α-L antigens and α-L antibodies containing the α-L antibody of claim 2 combined with fine particles.

5. A reagent for detecting α-L antigens and α-L antibodies containing the α-L antibody of claim 2, labelled with an isotope.

6. A reagent for detecting α-L antibodies and α-L antigens comprising an α-L antigen having the following properties:
    (1) Molecular Weight: About 1,000,000;
    (2) Electrophoretic mobility: In the $\beta$—$\alpha_2$ globulin region, which is an intermediate value between that of an HBs antigen and an α-fetoprotein;
    (3) Isoelectric point: PI = 5.04, the activity of the α-L antigen was shown in the range of 4.22 to 5.68 by measuring with an Ampholien column;
    (4) Bouyant Density: d = 1.08 g/ml in a solution of cesium chloride; and d = 1.03 g/ml in a solution of sucrose;
    (5) Formation of complex: A precipitable complex is formed with dextran sulfate in the presence of magnesium chloride, exhibiting lipoprotein-like properties;
    (6) Staining: The α-L antigen/antibody precipitated line in agar gel can be stained with Sudan black B;
    (7) Thermostability: The antigenic properties in the serum are maintained at a temperature of 56° C. for 30 minutes; and
    (8) Form (as an antigen/antibody complex): the spherical particles are about 300 Å in diameter.

7. A reagent for detecting α-L antigens and α-L antibodies containing the α-L antigen of claim 6 in the form of a plate, said reagent prepared by dissolving the α-L antigen in a liquid together with a supporting medium and solidifying the resulting solution in the form of a plate.

8. A reagent for detecting α-L antibodies and α-L antigens comprising the α-L antigen of claim 6 combined with fine particles.

9. A reagent for detecting α-L antibodies and α-L antigens comprising the α-L antigen of claim 6, labelled with an isotope.

10. A method for the purification of an α-L antigen which comprises preparing a solution of an α-L antigen and subjecting said solution to a density gradient centrifugation to collect a fraction having a buoyant density less than 1.1 g/ml, said α-L antigen having the following properties:

(1) Molecular weight: About 1,000,000;
(2) Electrophoretic mobility: In the $\beta$—$\alpha_2$ globulin region, which is an intermediate value between that of an HBs antigen and an $\alpha$-fetoprotein;
(3) Isoelectric point: PI = 5.04, the activity of the $\alpha$-L antigen was shown in the range of 4.22 to 5.68 by measuring with an Ampholien column;
(4) Bouyant Density: d = 1.08 g/ml in a solution of cesium chloride; and d = 1.03 g/ml in a solution of sucrose;
(5) Formation of complex: A precipitable complex is formed with dextran sulfate in the presence of magnesium chloride, exhibiting lipoprotein-like properties;
(6) Staining: The $\alpha$-L antigen/antibody precipitated line in agar gel can be stained with Sudan black B;
(7) Thermostability: The antigenic properties in the serum are maintained at a temperature of 56° C. for 30 minutes; and
(8) Form (as an antigen/antibody complex): the spherical particles are about 300 Å in diameter.

11. A method according to claim 10, wherein cesium chloride is used as a medium in the density gradient centrifugation step.

* * * * *